(12) United States Patent
Bi

(10) Patent No.: US 9,474,875 B2
(45) Date of Patent: Oct. 25, 2016

(54) BYPASS APPARATUS FOR AN ABSORPTION TANK

(71) Applicant: Beijing Aeonmed Co., Ltd., Beijing (CN)

(72) Inventor: Huimin Bi, Beijing (CN)

(73) Assignee: Beijing Aeonmed Co., Ltd., Beijing (CN)

( * ) Notice: Subject to any disclaimer, the term of this patent is extended or adjusted under 35 U.S.C. 154(b) by 191 days.

(21) Appl. No.: 14/000,596

(22) PCT Filed: Dec. 25, 2012

(86) PCT No.: PCT/CN2012/087357
§ 371 (c)(1),
(2) Date: Oct. 9, 2013

(87) PCT Pub. No.: WO2013/097680
PCT Pub. Date: Jul. 4, 2013

(65) Prior Publication Data
US 2014/0069539 A1   Mar. 13, 2014

(30) Foreign Application Priority Data

Dec. 30, 2011  (CN) .......................... 2011 1 0456166

(51) Int. Cl.
*A61M 16/20* (2006.01)
*A61M 16/22* (2006.01)
*A61M 16/08* (2006.01)

(52) U.S. Cl.
CPC ......... *A61M 16/20* (2013.01); *A61M 16/0891* (2014.02); *A61M 16/22* (2013.01);
(Continued)

(58) Field of Classification Search
CPC ........... A61M 16/20; A61M 16/0891; A61M 16/22; A61M 2205/12; A61M 16/201; A61M 2205/7581; Y10T 137/86493; Y10T 137/86726

USPC ........... 128/205.24, 205.12, 205.27–205.28; 251/251–263, 143, 144, 149.3; 137/625.29
See application file for complete search history.

(56) References Cited

U.S. PATENT DOCUMENTS 6,186,162 B1 *  2/2001  Purvis et al. ................. 137/312
6,289,890 B1 *  9/2001  Bliss et al. ............... 128/203.11
(Continued)

FOREIGN PATENT DOCUMENTS

CN  201008692 Y  1/2008
CN  101310790 A  11/2008
(Continued)

OTHER PUBLICATIONS

CN101310790 Machine Translation, Retrieved Feb. 10, 2016.*
(Continued)

*Primary Examiner* — Michael R Reid
(74) *Attorney, Agent, or Firm* — Venable LLP; Henry J. Daley

(57) ABSTRACT

A bypass device for an absorption tank comprises a two-position three-way valve, a micro switch, a control circuit board, and a micro switch actuation mechanism. When an absorption tank needs to be replaced, in the process of rotating a handle, a contact wheel of the micro switch is pressed to send an electrical signal to the control circuit board, and the control circuit board controls a solenoid valve, thereby controlling a gas path of the two-position three-way valve, and bypassing the absorption tank effectively and timely. After the absorption tank is replaced, it is only required to rotate the handle to the original position, so that the entire replacement process involves simple operations and is effective, and the sealing effect of the gas path is desirable.

14 Claims, 5 Drawing Sheets

(52) U.S. Cl.
CPC ....... *A61M 16/201* (2014.02); *A61M 2205/12* (2013.01); *A61M 2205/7581* (2013.01); *Y10T 137/86493* (2015.04)

(56) References Cited

U.S. PATENT DOCUMENTS

| | | | |
|---|---|---|---|
| 6,328,036 B1 | 12/2001 | Emtell et al. | |
| 2004/0103894 A1 | 6/2004 | Loncar | |
| 2008/0114289 A1* | 5/2008 | Muri et al. | 604/30 |
| 2009/0056720 A1* | 3/2009 | Chen et al. | 128/205.28 |
| 2010/0071698 A1* | 3/2010 | Kiritake | 128/205.27 |

FOREIGN PATENT DOCUMENTS

| | | |
|---|---|---|
| CN | 201840746 U | 5/2011 |
| CN | 102114289 A | 7/2011 |
| CN | 202010354 U | 10/2011 |

OTHER PUBLICATIONS

International Search Report issued in International Application No. PCT/CN2012/087357 dated Apr. 4, 2013.

* cited by examiner

--Prior Art--

--Prior Art--

BYPASS APPARATUS FOR AN ABSORPTION TANK

TECHNICAL FIELD

The present invention relates to a bypass apparatus, more specifically, to an air path control technology for replacing an absorption tank in a circuit and a corresponding mechanical structure.

TECHNICAL BACKGROUND

In the prior art, a purely mechanical control technology is used for the placement of an absorption tank in a circuit by mainly two manners. In the first one of the manners, an air path is switched by turning a switch in the air path, and then the absorption tank is detached for the replacement of the absorption tank; and in the other one of the manners, the air path is switched by means of a bypass valve. The air path may be switched directly by a pneumatic switch during a surgery; in some cases, the absorption tank is replaced until the surgery is finished. Due to a manual operation of the switch, the replacement operation is inconvenient.

The first air path control technology for the placement of the absorption tank in the circuit is achieved by a manual reversing valve shown in FIG. 8A. During the normal working conditions, the manual reversing valve is at its position 1, and the air exhaled by a patient flows into the absorption tank; when the absorption tank is required to be replaced, the manual reversing valve is turned to its position 2, and then the air exhaled by the patient directly flows into an absorption circuit without passing through the absorption tank. Due to a manual operation of the switch, a misoperation may be likely caused, that is, it is likely to forget the operation on the manual reversing valve during the removal of the absorption tank, thus causing the temporary open of the air path.

The second air path control technology for the placement of the absorption tank in the circuit is achieved by two spring-return typed two-position three-way valves shown in FIG. 8B. During the normal working conditions, the springs are pressed by the absorption tank and those two two-position three-way valves are at their positions 2, and the air exhaled by a patient flows into the absorption tank; if the absorption tank is required to be replaced, the spring is returned when the absorption tank is removed, and the two-position three-way valves are at their positions 1, and then the air exhaled by the patient flows into an absorption circuit without flowing into the absorption tank. This technology is very demanding for the sealing and coaxiality between two air channel openings of the absorption tank and the two-position three-way valves when the absorption tank is mounted, and poor mounting easily causes an air leakage.

SUMMARY OF THE INVENTION

In view of the above technical problem in the prior art, an object of the present invention is to provide a bypass apparatus for an absorption tank, for the purpose of an easy and effective process of replacing the absorption tank and a good sealing effect of the air path.

The present invention is achieved by the following technical solution.

A bypass apparatus for an absorption tank includes:

a two-position three-way valve, which is used to connect the absorption tank with a circuit at its first position, and bypass the absorption tank at its second position;

a microswitch, which has a first state corresponding to the first position of the two-position three-way valve, and a second state corresponding to the second position of the two-position three-way valve;

a control circuit board, which is used to switch the two-position three-way valve between the first position and the second position in response to a state change of the microswitch; and an actuating mechanism of the microswitch, which is used to switch the microswitch between the first state and the second state.

Preferably, the actuating mechanism of the microswitch is a cam mechanism including:

a cam, which is rotatable around a cam shaft;

a cam base, which is used for assembling the cam and the cam shaft; and a driven part, which is in contact with an edge of the cam, and is used to actuate the microswitch in response to the rotation of the cam.

Preferably, the driven part is a supporting pipe for supporting the absorption tank.

Preferably, the supporting pipe can slide between a first end position and a second end position in response to the rotation of the cam, and when the supporting pipe is at the first end position, the absorption tank is in a state of being supported by the supporting pipe; and when the supporting pipe is at the second end position, the absorption tank is in a detached state.

Preferably, the supporting pipe is located below the absorption tank.

Preferably, a handle for driving the cam is arranged on the cam shaft.

Preferably, the driven part is one of a roller type.

Preferably, the microswitch includes a contacting part in contact with the actuating mechanism of the microswitch.

Preferably, the contacting part is a contacting wheel.

Preferably, the two-position three-way valve is an electromagnetic valve.

According to the above technical solution, the beneficial effects of the present invention lie in that: if an absorption tank is required to be replaced, the contacting wheel of the microswitch is pressed to transmit an electrical signal to the control circuit board when the handle is rotated, and the control circuit board controls the electromagnetic valve and hence controls the air path of the two-position three-way valve, thereby effectively and timely bypassing the absorption tank by such a convenience and time-saving operation. After the absorption tank is replaced, it is only required to move the handle back to its initial position. Therefore, the operation of the entire replacement process is easy and effective, and a good sealing effect of the air path is ensured.

Figure 1:
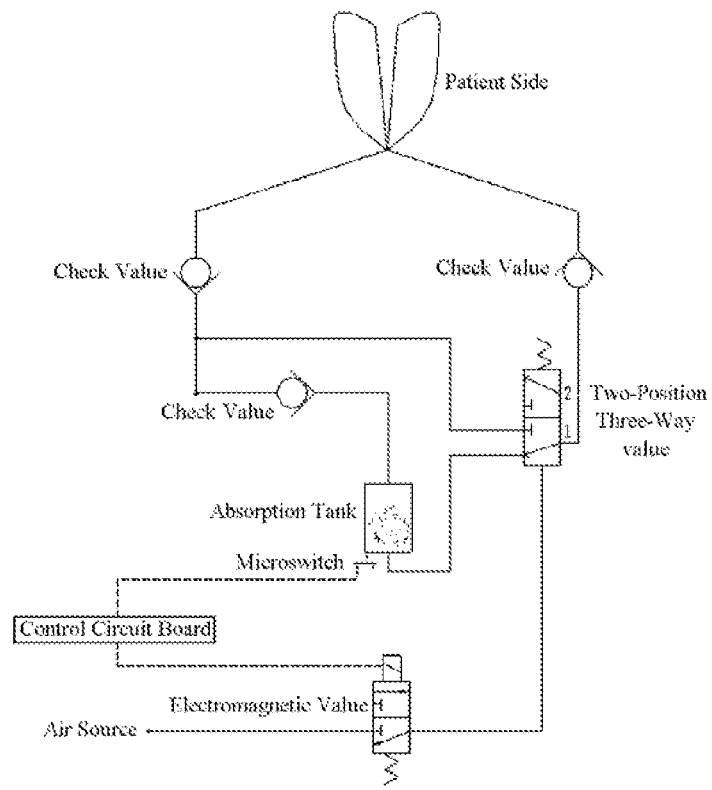
FIG. 1 is a schematic diagram showing a bypass apparatus for an absorption tank applied to an air flow circuit of a patient.

A list of reference numerals:

| | | | |
|---|---|---|---|
| 1: Cam; | 2: Limit stud; | 3: Left bearing; | 4: Handle; |
| 5: Left gasket; | 6: Cam base; | 7: Sliding sleeve; | 8: Beam; |
| 9: Limit pin; | 10: Supporting pipe; | 11: Roller; | 12: Shaft sleeve; |
| 13: Pin shaft; | 14: Right gasket; | 15: Right bearing; | 16: Handle; |
| 17: Fastening screw; | 18: Microswitch; | 19: Supporting plate; | 20: Absorption tank; |
| 21: Connecting plate; | 22: Contacting wheel; | 23: Hexagonal socket head screw. | |
| 24: Cam shaft. | | | |

DETAILED DESCRIPTION OF THE PREFERRED EMBODIMENT

The present invention will be further described by way of embodiments below in conjunction with the accompanying drawings, which should not be interpreted as a limit to the present invention.

Figure 2:
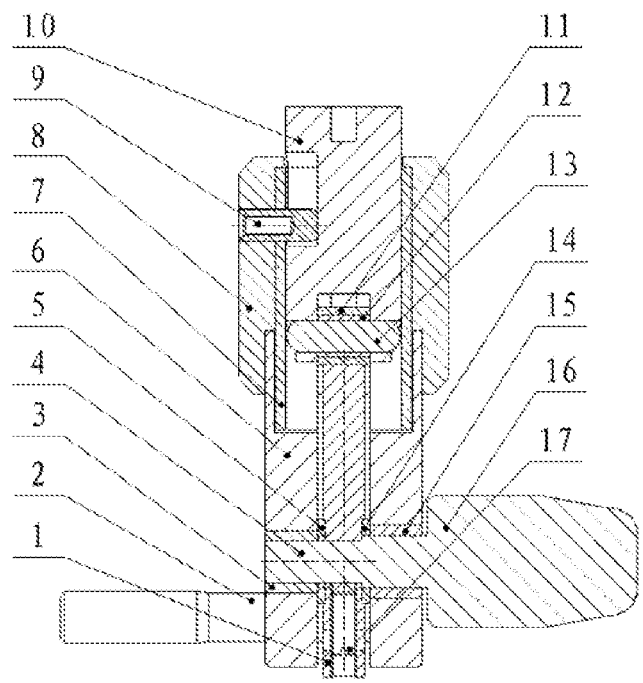
FIG. 2 is a schematic diagram showing the cross-sectional structure of the bypass apparatus for an absorption tank.
Figure 3:
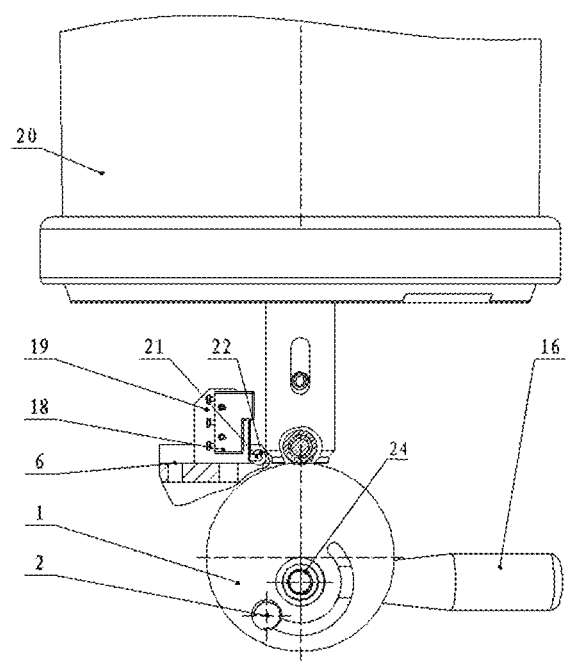
FIG. 3 is a front view of the bypass apparatus for an absorption tank.
Figure 5:
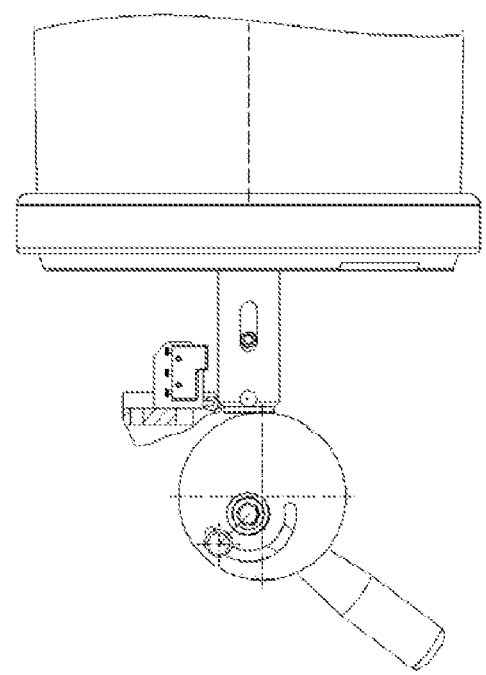
FIG. 5 is a schematic diagram of the bypass apparatus for an absorption tank when the absorption tank is in a detached state.

FIGS. 1 and 2 show the constitution structure of a bypass apparatus for an absorption tank. A microswitch 18 is connected with a contacting wheel 22 by a connecting plate 21. In a normal operation, an absorption tank 20 is positioned in relation to a supporting pipe 10 as shown in FIG. 3, the contacting wheel 22 is not contacted with the supporting pipe 10, and air exhaled by a patient flows into the absorption tank 20 through a check valve and flows into an inhalation end (as shown in FIG. 1) of the patient after being cleaned by the absorption tank. When the absorption tank is required to be replaced by an operator, a cam 1 is rotated about a cam shaft 24 to a position as shown in FIG. 5 by rotating a handle 16, so that the absorption tank 20 is lowered, the lower end of the supporting pipe 10 is contacted with the contacting wheel 22, and the microswitch 18 is pressed to transmit an electrical signal to a control circuit board, which in turn transmits a signal to an electromagnetic valve; in this case, the power provided to the electromagnetic valve is cut off and hence no driving gas is provided for a two-position three-way valve, thus a second path is closed and a first path is open in the two-position three-way valve, the air exhaled by the patient passes through the second path of the two-position three-way valve, and then flows into an inhalation end of the patient, without passing through the absorption tank 20. Therefore, the absorption tank is bypassed for easy replacement by the operator.

To achieve the positioning by the handle 16, a cam base 6 is fixed to a beam 8 by a screw, a left gasket 5 and a right gasket 14 are respectively arranged in grooves of the cam 1, a left bearing 3 and a right bearing 15 are respectively arranged in the respective holes in the cam base 6 by an interference fit manner, then the handle 16 is inserted into the bearings and the corresponding hole in the cam 1, and a fastening screw 17 is screwed into a screw hole in the cam 1.

A sliding sleeve 7 is arranged in the beam 8 by an interference fit manner, a pin shaft 13 is arranged in a shaft sleeve 12 by an interference fit manner and then is inserted into corresponding holes of the supporting pipe 10 and a roller 11, then the supporting pipe 10 is inserted into the sliding sleeve 7, and a limit pin 9 is inserted into corresponding holes of the beam 8 and the sliding sleeve 7 by an interference fit manner.

The connecting plate 21 and the contacting wheel 22 are connected with the microswitch 18 by a screw, the microswitch 18 is connected with a supporting plate by two hexagonal socket head screws (M1.6×6), and the supporting plate 19 is fixed to the top surface of the cam base 6 by a hexagonal socket head screw 23.

Figure 4:
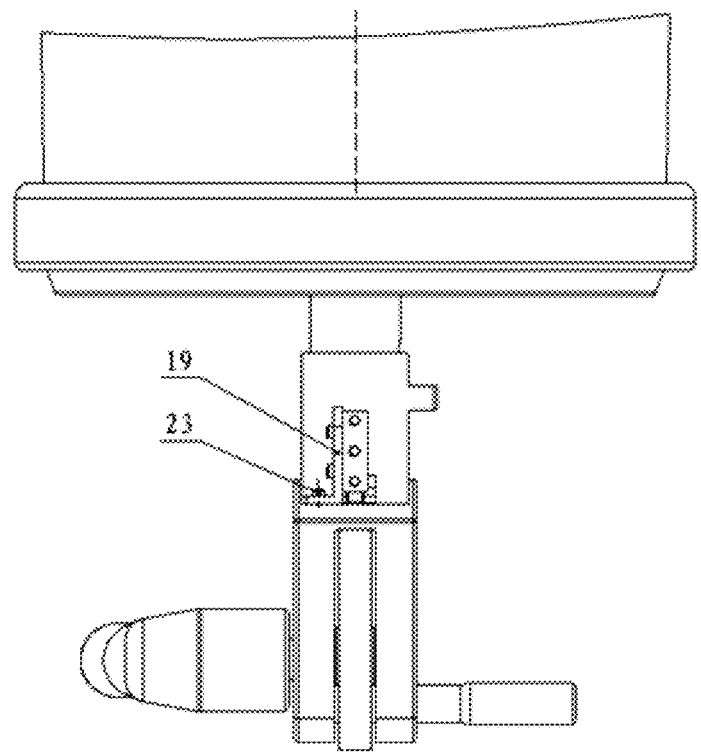
FIG. 4 is a left view of the bypass apparatus for an absorption tank.

FIGS. 3 to 5 show the working process of the bypass apparatus for an absorption tank according to the present invention.

In a practical application, to replace the absorption tank 20 as required, the handle 16 is rotated from a position as shown in FIG. 3 to a position as shown in FIG. 5, thus the contacting wheel 22 is subject to the pressure by the supporting pipe 10, and the microswitch 18 transmits an electrical signal to the control circuit board, which in turn is used to cut off the power for the electromagnetic valve, thus the second path is closed and the first path is open in the two-position three-way valve, and hence the air exhaled by a patient does not pass through the absorption tank 20, which may be then easily replaced. After the absorption tank has been replaced, the handle 16 is rotated from the position as shown in FIG. 5 back to the position as shown in FIG. 3, in this case, the contacting wheel 22 is detached from the supporting pipe 10, and the microswitch 18 transmits an electrical signal to the control circuit board, which in turn power on the electromagnetic valve, so that the first path is closed and the second path is open in the two-position three-way valve, and the air exhaled by the patient passes through the absorption tank 20 to resume the normal operation.

Figure 6:
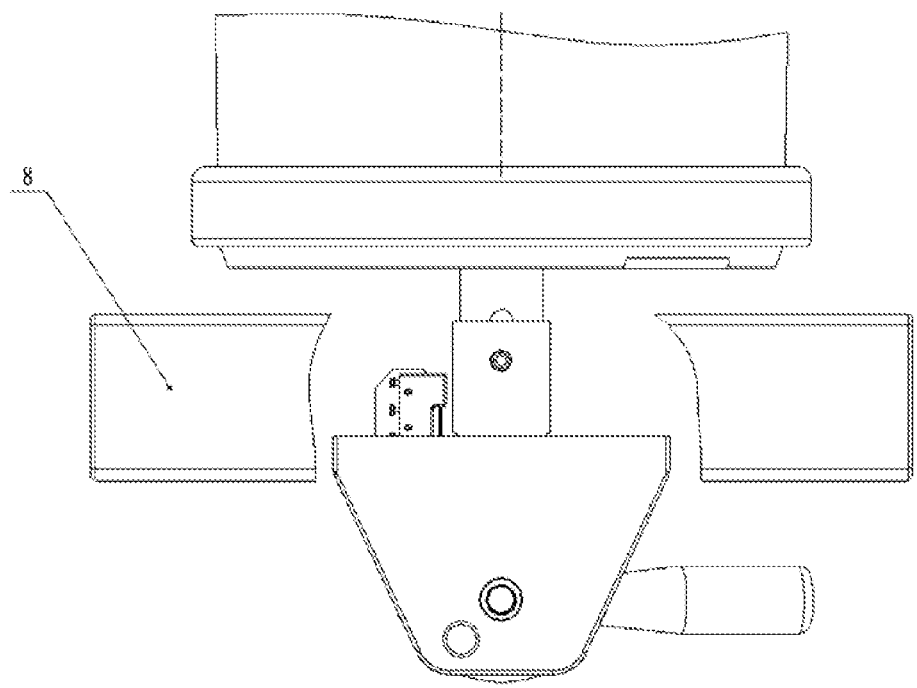
FIG. 6 is a schematic diagram of the bypass apparatus for an absorption tank according to another embodiment.
Figure 7:
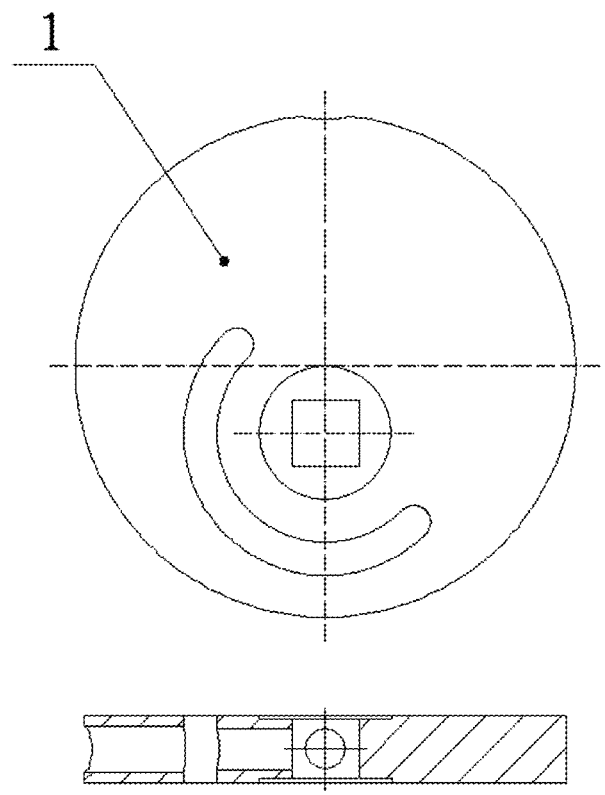
FIG. 7 is a diagram showing parts of a cam of the bypass apparatus for an absorption tank.
Figure 8A:
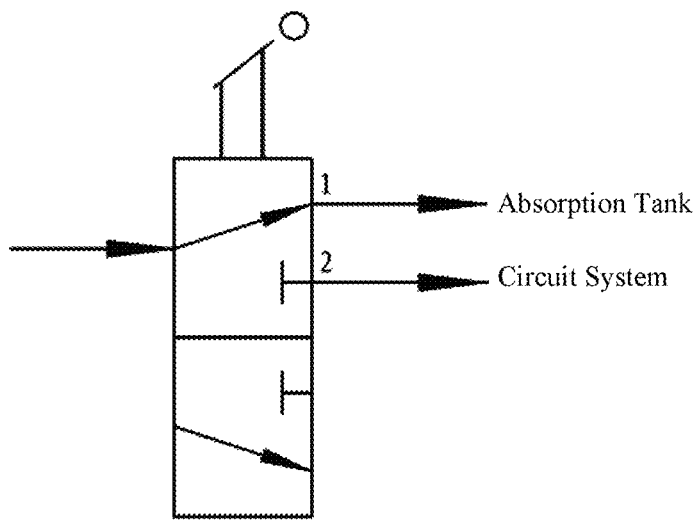
FIGS. 8A and 8B are schematic diagrams showing manners of replacing the absorption tank in the prior art.
Figure 8B:
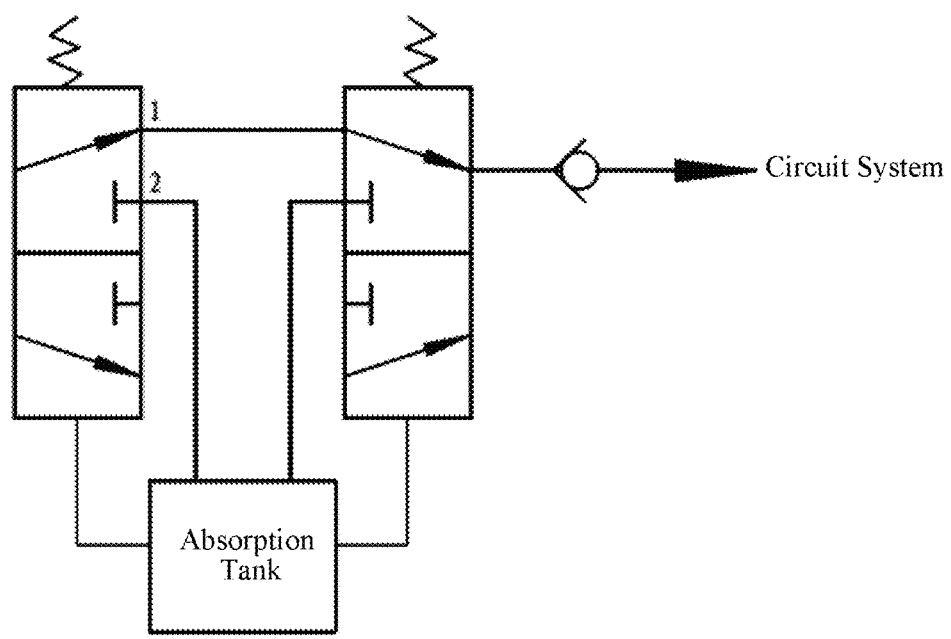

Alternatively, the contacting wheel 22 and the supporting pipe 10 also may have shapes other than those shown in the drawings. The contacting wheel 22 may have, for example, a cam-like shape, a spherical shape, etc., as shown in FIG. 6.

Alternatively, the bypass structure of the present invention also may be applied to other products, systems or technical fields requiring for bypass.

The preferred embodiments of the present invention has been described as above to explain the technical solution and inventive concept of the present invention, but not to limit the protection scope of the claims of the invention. For those skilled in the art, any other technical solutions, which may be obtained through logical analysis, deduction or definite experiments in conjunction with the prior art based on inventive concept of the present invention, should be included within the protection scope of the claims of the present invention.

The invention claimed is:

1. A bypass apparatus for an absorption tank, comprising:
    a two-position three-way valve having a first position to connect the absorption tank with a circuit and a second position to bypass the absorption tank;
    a microswitch having a first state corresponding to the first position of the two-position three-way valve, and a second state corresponding to the second position of the two-position three-way valve;
    a control circuit to switch the two-position three-way valve between the first position and the second position in response to a state change of the microswitch; and
    an actuating mechanism coupled to the microswitch to switch the microswitch between the first state and the second state, wherein the actuating mechanism includes a cam mechanism, comprising:
- a cam shaft and a cam rotatable around the cam shaft,
- a cam base for assembling the cam and the cam shaft, and
- a driven part in contact with an edge of the cam to actuate the microswitch in response to a rotation of the cam.

2. The bypass apparatus for an absorption tank of claim 1, wherein, the driven part comprises a supporting pipe for supporting the absorption tank.

3. The bypass apparatus for an absorption tank of claim 2, wherein, the supporting pipe slides between a first end position and a second end position in response to the rotation of the cam, and when the supporting pipe is at the first end position, the absorption tank is in a state of being supported by the supporting pipe; and when the supporting pipe is at the second end position, the absorption tank is in a detached state.

4. The bypass apparatus for an absorption tank of claim 2, wherein, the supporting pipe is located below the absorption tank.

5. The bypass apparatus for an absorption tank of claim 1, wherein, a handle for driving the cam is arranged on the cam shaft.

6. The bypass apparatus for an absorption tank of claim 1, wherein, the microswitch includes a contacting part in contact with the actuating mechanism of the microswitch.

7. The bypass apparatus for an absorption tank of claim 6, wherein, the contacting part is a contacting wheel.

8. The bypass apparatus for an absorption tank of claim 1, wherein, the two-position three-way valve is an electromagnetic valve.

9. The bypass apparatus for an absorption tank of claim 3, wherein, the supporting pipe is located below the absorption tank.

10. The bypass apparatus for an absorption tank of claim 2, wherein, a handle for driving the cam is arranged on the cam shaft.

11. The bypass apparatus for an absorption tank of claim 3, wherein, a handle for driving the cam is arranged on the cam shaft.

12. The bypass apparatus for an absorption tank of claim 1, wherein, the microswitch includes a contacting part in contact with the actuating mechanism of the microswitch.

13. The bypass apparatus for an absorption tank of claim 12, wherein, the contacting part is a contacting wheel.

14. The bypass apparatus for an absorption tank of claim 1, wherein, the control circuit includes a control circuit board coupled to an output of the microswitch and an electromagnetic valve having an input coupled to an output of the circuit board and an output coupled to the two-position three-way valve, wherein delivery of power to the electromagnetic valve is controlled by the circuit board in dependence on the state of the microswitch, and the position of the two-position three-way valve is controlled as a function of the output of the electromagnetic valve which changes in direct response to the output of the control circuit board.

* * * * *